United States Patent
Dyke

[11] Patent Number: 6,135,981
[45] Date of Patent: Oct. 24, 2000

[54] PROTECTIVE AORTIC OCCLUSION CATHETER

[76] Inventor: Charles C. Dyke, 1612 Jonquil Ave., McAllen, Tex. 78501

[21] Appl. No.: 08/955,591

[22] Filed: Oct. 22, 1997

[51] Int. Cl.[7] .................................................. A61M 29/00
[52] U.S. Cl. .................................. 604/96.01; 604/101.01; 606/194
[58] Field of Search ............................... 604/96, 101, 102, 604/103, 53, 49; 606/191, 192, 194, 195

[56] References Cited

U.S. PATENT DOCUMENTS

| | | | |
|---|---|---|---|
| Re. 35,352 | 10/1996 | Peters | 604/4 |
| 3,971,385 | 7/1976 | Corbett | 128/351 |
| 4,248,224 | 2/1981 | Jones | 128/214 R |
| 4,459,977 | 7/1984 | Pizon et al. | 128/1 D |
| 4,531,935 | 7/1985 | Berryessa | 604/45 |
| 4,798,588 | 1/1989 | Aillon | 604/122 |
| 4,804,359 | 2/1989 | Grunwald et al. | 604/4 |
| 5,002,532 | 3/1991 | Gaiser et al. | 604/101 |
| 5,021,045 | 6/1991 | Buckberg et al. | 604/53 |
| 5,074,845 | 12/1991 | Miraki et al. | 604/101 |
| 5,197,952 | 3/1993 | Marcadis et al. | 604/96 |
| 5,324,260 | 6/1994 | O'Neill et al. | 604/96 |
| 5,344,399 | 9/1994 | Devries | 604/96 |
| 5,385,548 | 1/1995 | Williams et al. | 604/96 |
| 5,395,330 | 3/1995 | Marcadis et al. | 604/96 |
| 5,395,331 | 3/1995 | O'Neill et al. | 604/96 |
| 5,415,635 | 5/1995 | Bagaoisan et al. | 604/96 |
| 5,423,745 | 6/1995 | Todd et al. | 604/53 |
| 5,443,448 | 8/1995 | Devries | 604/96 |
| 5,458,574 | 10/1995 | Machold et al. | 604/101 |
| 5,460,610 | 10/1995 | Don Michael | 606/192 X |
| 5,484,412 | 1/1996 | Pierpont | 604/101 |
| 5,487,730 | 1/1996 | Marcadis et al. | 604/96 |
| 5,505,698 | 4/1996 | Booth et al. | 604/96 |
| 5,556,412 | 9/1996 | Hill | 606/194 |
| 5,588,965 | 12/1996 | Burton et al. | 606/192 X |
| 5,674,198 | 10/1997 | Leone | 604/101 |
| 5,728,068 | 3/1998 | Leone et al. | 604/101 |
| 5,810,757 | 9/1998 | Sweezer, Jr. et al. | 604/96 X |

*Primary Examiner*—John D. Yasko

[57] ABSTRACT

A method and apparatus for occluding a patient's aorta during open heart surgery uses a cannula with a distal end carrying two expandable members or balloons. One balloon is a total occlusion balloon, the other a partial occlusion balloon. The balloons can be separately inflated and deflated. The cannula has multiple functions, such as a bypass portion for transmitting flow when the balloons have been expanded. Another cannula function is the administering of myocardial protecting solutions to the patient's heart.

8 Claims, 8 Drawing Sheets

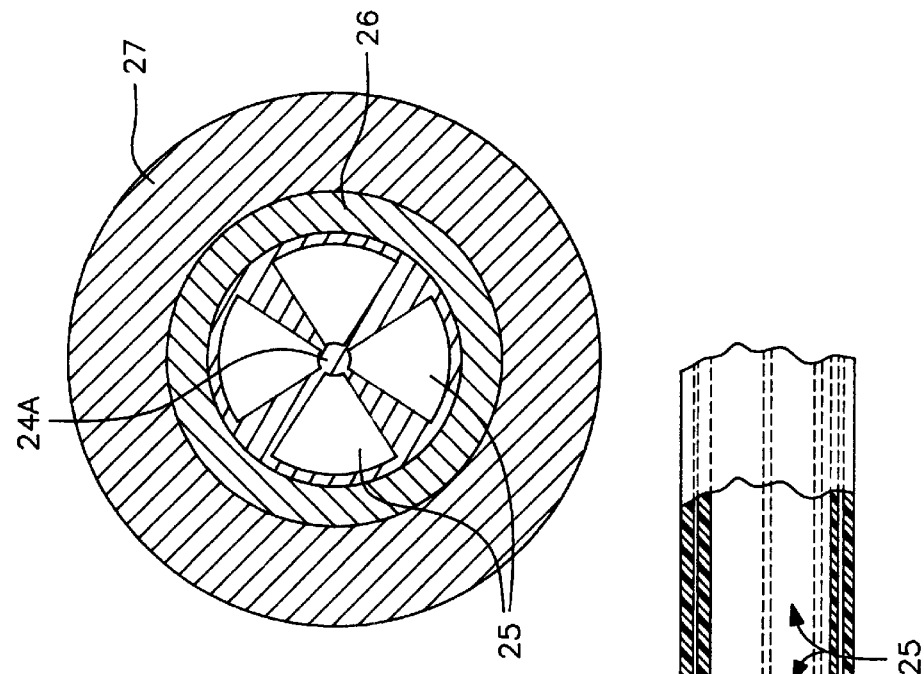
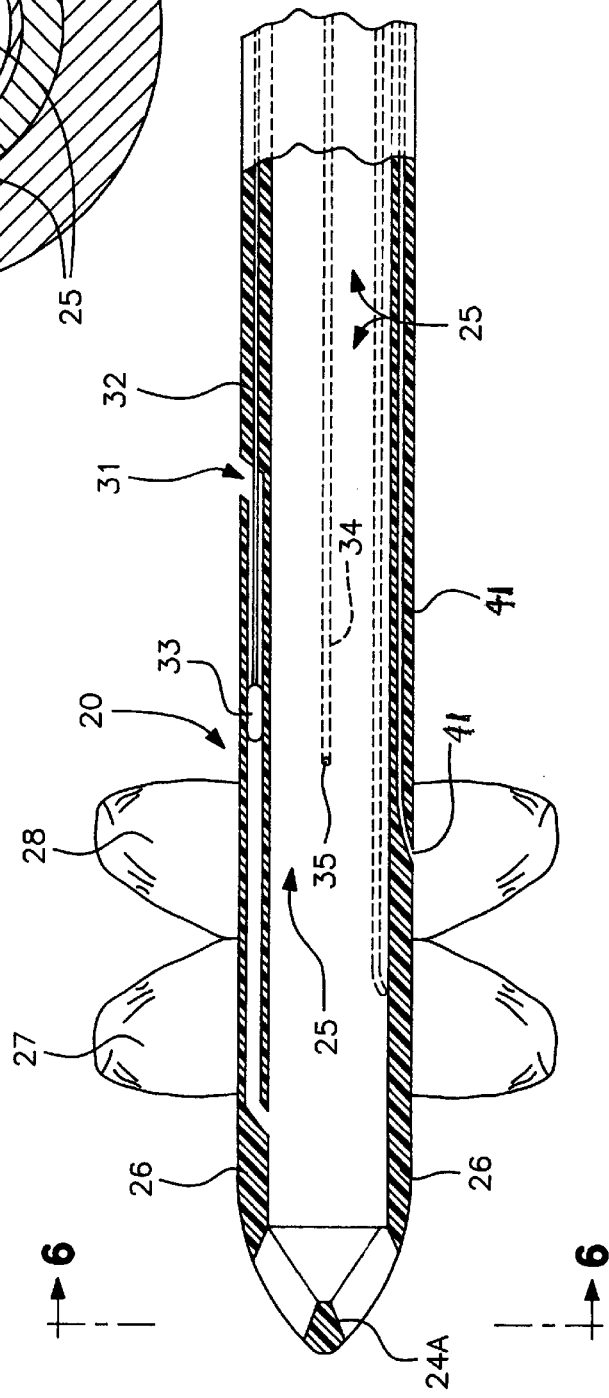
FIG. 6
FIG. 5

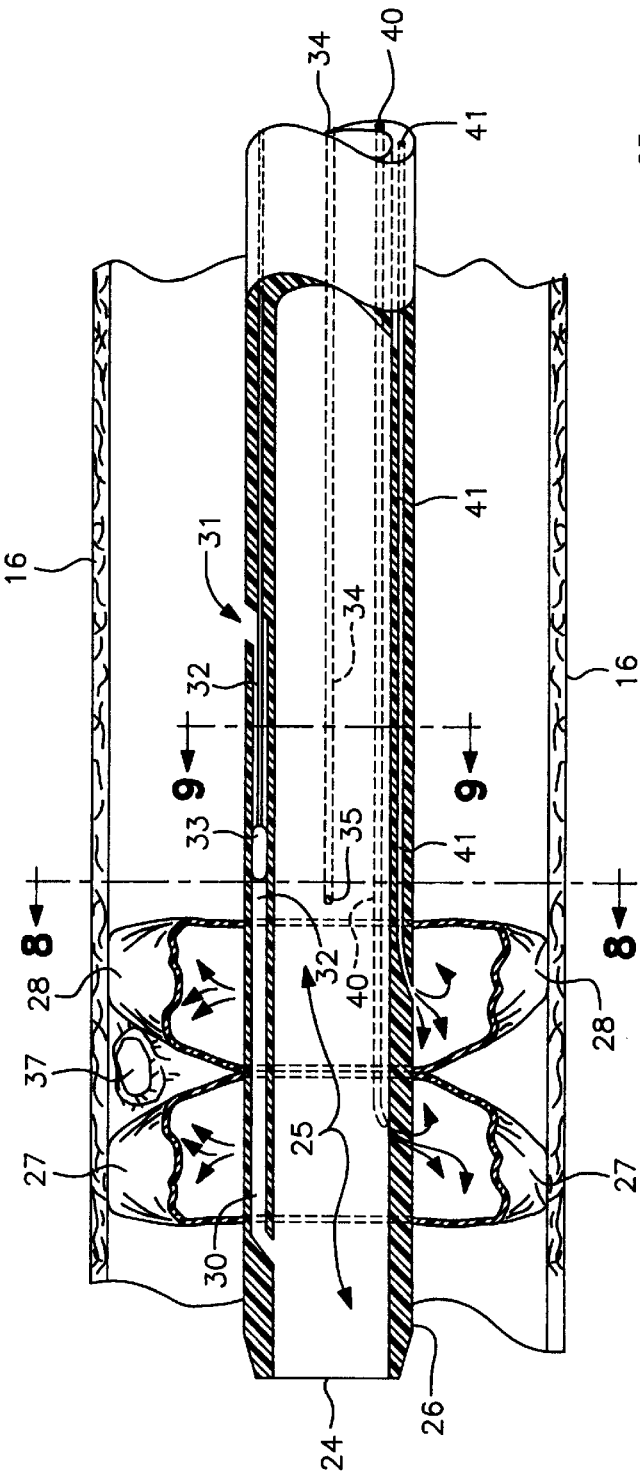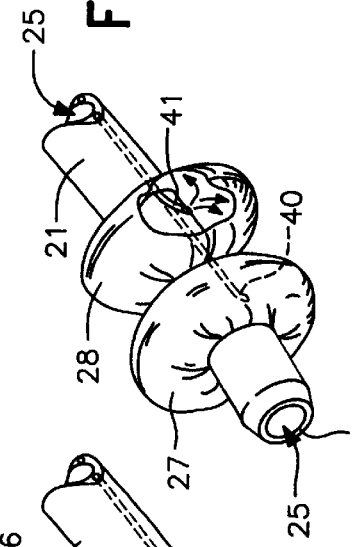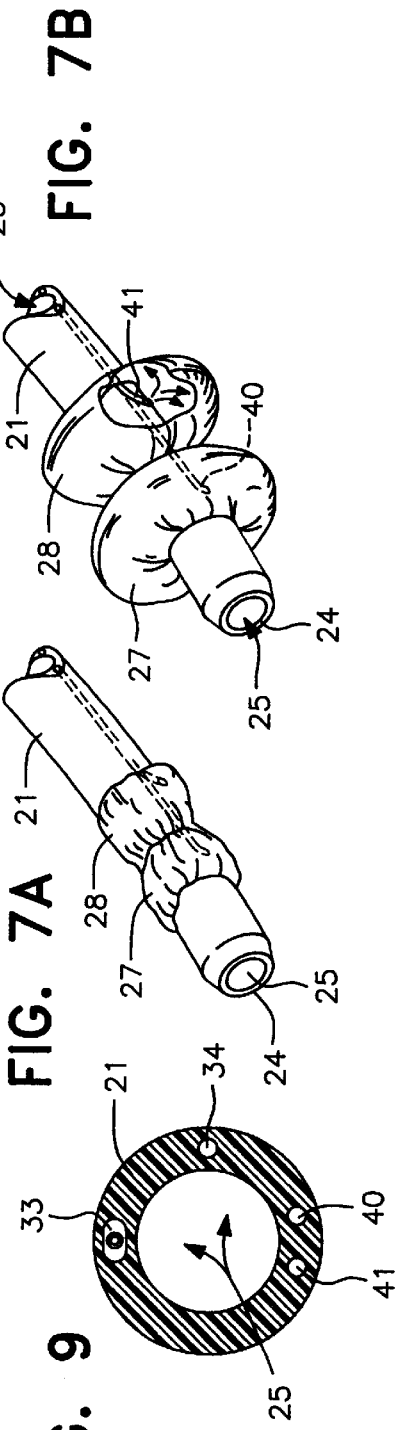

PROTECTIVE AORTIC OCCLUSION CATHETER

CROSS-REFERENCE TO RELATED APPLICATIONS

Not applicable.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to heart surgery and to cannulae used in heart surgery. The present invention relates to an improved surgical cannula, particularly a multifunctional aortic cannula. Even more particularly, the present invention relates to an improved multifunctional aortic cannula useful for open heart surgery, specifically during partial and total occlusion of the ascending aorta.

2. General Background of the Invention

Open heart procedures require flow from the heart to be interrupted to facilitate and improve operative field visibility. The present accepted practice is referred to as "cross clamping". "Cross clamping" accomplishes this task but can be damaging to the aortic structures and tissues and has potentially serious side effects.

Currently nearly all institutions use an externally applied metal occlusion clamp to occlude the aorta during open heart operations. This technique was considered to be satisfactory until information was gathered indicating that calcium from the inner wall of the aorta may become dislodged when the external clamp is applied and removed possibly causing strokes, paralysis, tissue necrosis and in some cases death.

The aortas which are heavily calcified must be treated very carefully. This danger for heart surgery patients of calcium fragments being knocked loose and causing an embolism damage to the brain and other important tissues equates into the fact that heart surgeons must treat these aortic tissues very carefully during surgery. The less manipulation and deformation these calcified aortas receive the less likely this calcium could become dislodged within the aorta. This cannula invention design will provide protection against this current problem. Surgeons have to deal with this threat to their open heart patients daily since a safer technology has not been developed, until now.

Another serious problem the patient currently must tolerate is the damage the metal occlusion clamps create by the severe unnatural deformation and stiff crushing forces that the aortas must endure.

The need therefore exists to reduce these serious problems and the associated trauma while still allowing the heart surgeon to fully or partially occlude the aorta during open heart operations performed through a sternotomy incision.

The only prior art device which attempts to solve this problem uses aortic occlusive balloon (AOB) principles, but is limited in several fundamental respects. The most significant of these problems is that the previous AOBs have no partial occlusion capabilities which this invention eliminates. Prior art devices with AOB technology are specifically designed to be introduced through a femoral catheter. Femoral insertion and placement of aortic occlusive balloon catheters increase significantly the danger of lower limb circulatory complications. Femoral catheter placement exactly into the aortic root is difficult to confirm. Correct placement must be verified with flouroscopy and/or transeophogeal echo. Femorally introduced catheter style AOBs are prone to migration within the aorta during the procedure which can cause potentially lethal side effects since continuous placement verification is necessary but is not practiced due to the technical and time constraints. The femorally introduced catheter is not designed to be introduced into the aorta under direct visualization as is this invention which eliminates the migration problems associated with previous technologies. This invention eliminates the danger and placement problems associated with femorally introduced aortic occlusion balloons which also lack the ability to partially occlude the aorta as this new technology will accomplish. Placement of this aortic occlusive balloon cannula is more accurate and safer than prior art AOBs, since the present invention is a cannula that is better secured. Optimal placement is accomplished by being physically palpated by the surgeon, and is verified under direct visualization.

Previous AOB catheters are not capable of protecting the aorta from the trauma of being overdistended especially applicable to older fragile thin walled aortas which may easily develop into an intimal tear or wall dissection and/or even more dangerous aortic rupture and death.

BRIEF SUMMARY OF THE INVENTION

The present invention relates to a safer technology to improve the benefits for patients undergoing open heart procedures, specifically during partial and total occlusion of the ascending aorta. The multifunctional aortic cannula of the present invention is designed to minimize trauma to the patient's ascending aorta in several ways, exhibiting many benefits over previous technologies. Through one incision site in the aorta, (1) partial occlusion capability, which no previous technologies can accomplish, (2) total occlusion capability without the problem of balloon migration which no previous technologies can accomplish, (3) total systemic circulatory support, (4) delivery of myocardial protecting solutions and (5) venting and removal of all solutions from the heart and aortic root as well as (6) bypass flow capability during partial occlusion which when combined into this advanced cannula design provides enormous benefits to the patient undergoing open heart surgery.

One important benefit includes the provision of an aortic retaining sleeve that protects the aorta in a manner not possible with previous aortic occlusive balloon (AOB) technologies. This is accomplished by minimizing the danger of the aorta being over distended. The present invention prevents the potentially fatal side effects that are associated with femorally placed catheter type aortic occlusive balloons.

Another significant advantage of the present cannula invention provides both partial and total occulation of the aorta. Occlusion selection can be independently controlled externally for partial or total occlusion along with purging capability during proximal anastamosis completion.

All previous AOBs are long flexible catheters which are prone to migration within the aorta and are limited to being inserted femorally. This inherently makes placement difficult and time consuming, since this must be done using calculated measurement under fluoroscopy or transesophogeal echo and potentially dangerous errors in placement are more likely.

Aortic root cannula incisions are not required when using the cannula of the present invention, therefore one less incision into the aorta is needed. The central lumen of the cannula is for the return of systemic cardiopulmonary support. When the aortic occlusive balloons are inflated, the cannula is centered optimally within the lumen of the aorta, in order to maximize the cannula's laminar flow characteristics. More importantly this will reduce the possibility of jet lesions damaging the area near the cannula tip within the lumen of the aorta.

Myocardial protecting solutions can be administered directly into the aortic root through the administration port integrated into the body of the cannula. Such solutions as well as air may be evacuated from the heart and the proximal ascending aorta.

Near the tip of the cannula, one balloon when inflated with saline solution effectively occludes the ascending aorta while the second partial occlusion balloon serves as a backup total occlusion balloon while the bypass port balloon is inflated. This creates a backup total occlusion capability if needed since each balloon operates independently from the other. The area between the twin balloon configuration provides for the surgeon an optimal target with minimal deformation along the aorta on to which the proximal anastamosis may be attached.

The present invention provides an improved method for aortic occlusion. The cannulation site is prepared on the aorta by placing a pursestring suture and then creating an incision through which the cannula body of the present invention is carefully introduced and then routed into the ascending aorta. This is accomplished with the bypass port and aortic occlusion balloons deflated.

The partial flow bypass port lumen is carefully and completely de-aired before insertion and rechecked. The cannula is then positioned within the lumen of the ascending aorta distal to the coronary ostia, well proximal to the arch vessels at a site where the surgeon decides the proximal anastamosis will be approximated. The pursestring is then secured to the cannula body, holding it securely in place.

The partial occlusion balloon is partially inflated and palpated by the surgeon for positive placement.

The protective aortic sleeve is the positioned around the aorta circumferentially. Placement is verified by once more palpating the partially inflated partial occlusion balloon.

The partial occlusion balloon is then fully inflated along with the total occlusion balloon while the internal balloon pressures are monitored within the safe predesignated parameters. Occlusive aortic balloons must be filled using only sterile saline solution completely free of any air. The predesignated safe parameters for effective balloon inflation pressures are between about 250 to 400 torr (mm Hg). The aortic occlusion balloon maximum functional diameter should be between about 25–50 mm.

At this point the bypass flow port balloon is fully inflated thereby completely occluding the bypass port which will fully isolate the heart from the systemic circulation.

The myocardial protecting solution mixture is delivered to the section of the aorta which is proximal to the occlusive balloons through the cardioplegia delivery port.

Once a full arrest is attained and the antegrade cardioplegia dose has been administered, a controlling stopcock valve is turned enabling the aortic root and heart to be vented through the same port and channel through which the myocardial protecting solution was administered.

When the surgeon completes the necessary distal anastamosis, the heart and aortic root are filled with blood and completely de-aired.

The partial flow bypass port balloon is then deflated and partial bypass is commenced.

The surgeon then will complete the proximal anastamosis on the aorta within the region between the partial and the total occlusion balloons.

The protective aortic sleeve has a removable center section that can be peeled away to expose the section of the aorta for the proximal anastamosis site.

As the last proximal anastamosis is nearing completion, the partial occlusion balloon is slightly deflated to displace any air still proximal to the total occlusion balloon.

When all air has been purged, the partial occlusion balloon is first fully deflated, This is followed by the deflation of the total occlusion balloon.

The cardiac output and graft condition may be evaluated at this time after which cardiopulmonary bypass is terminated and the fully deflated cannula is then removed and pursestring tied off.

Examples of open heart procedures in which the catheter apparatus of the present invention will be effective include for example, coronary artery bypass procedures, redo coronary artery bypass procedures, mitral valve replacement procedures, redo mitral valve replacement procedures, mitral valve repair procedures, aortic valve replacement procedures, redo aortic valve replacement procedures, mitral valve repair procedures, left ventricular aneurysm procedures, atrial myxoma removal, as well as combinations of the above procedures and other like procedures.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 5 is a partial longitudinal sectional view of the preferred embodiment of the apparatus of the present invention;

FIG. 6 is a transverse sectional view taken along lines 6—6 of FIG. 5;

FIG. 7 is a sectional elevational view of a second embodiment of the apparatus of the present invention;

FIGS. 7A–7B are fragmentary views of the second embodiment of the apparatus of the present invention;

FIG. 9 is a sectional view taken along lines 9—9 of FIG. 7;

DETAILED DESCRIPTION OF THE INVENTION

Figure 1:
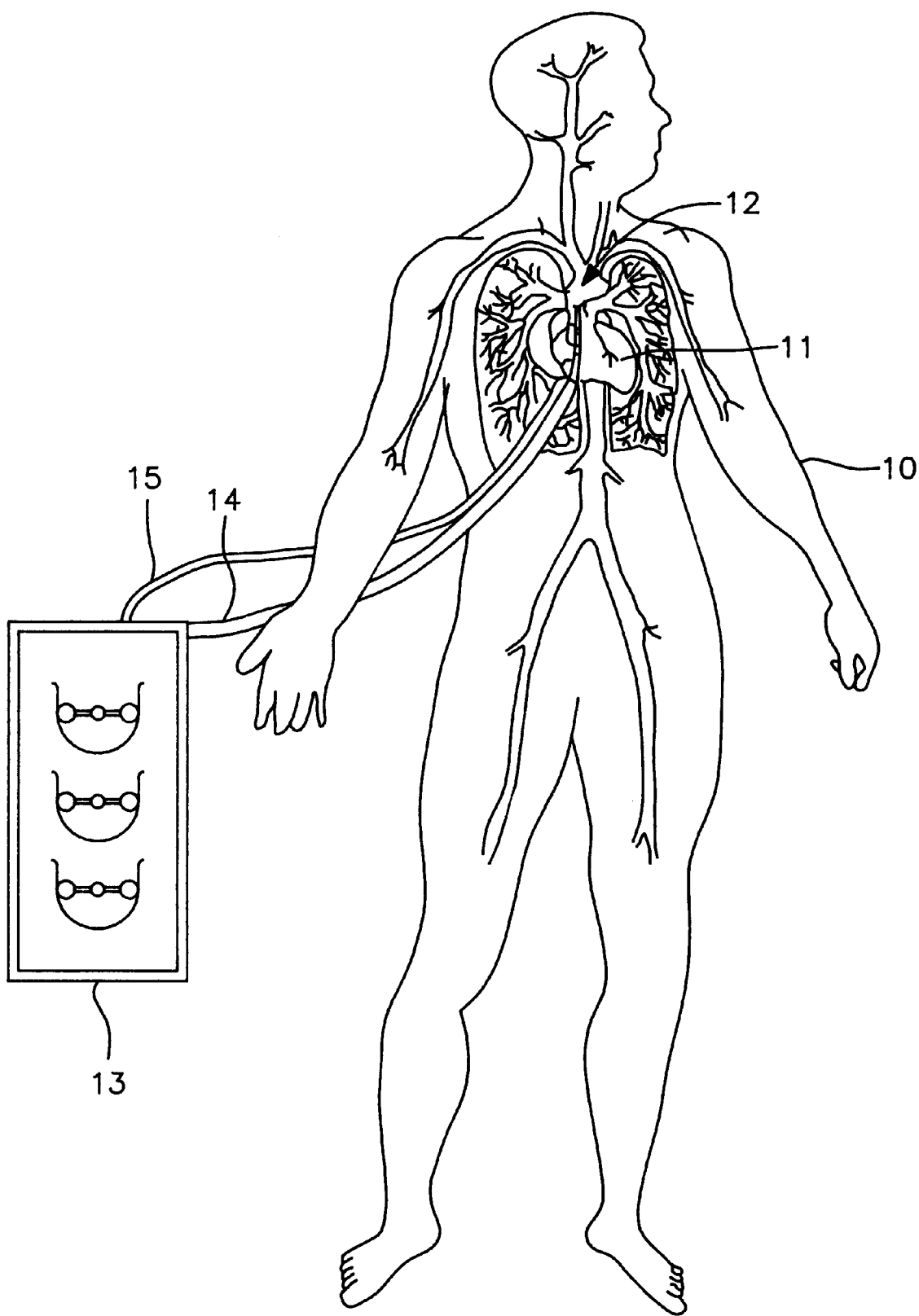
FIG. 1 is a schematic view illustrating a patient and cardiopulmonary bypass machine generally showing the method and apparatus of the present invention.

FIG. 1 shows a heart patient 10, the patient's heart 11, and a cannulation site 12. A cardiopulmonary bypass machine 13 is shown having a pair of flow lines 14, 15 for establishing fluid communication between the cbm machine 13 and the patient's heart 11 during open heart surgery. The flow line 14 is an arterial delivery line. The flow line 15 is venous return line.

Figure 2:
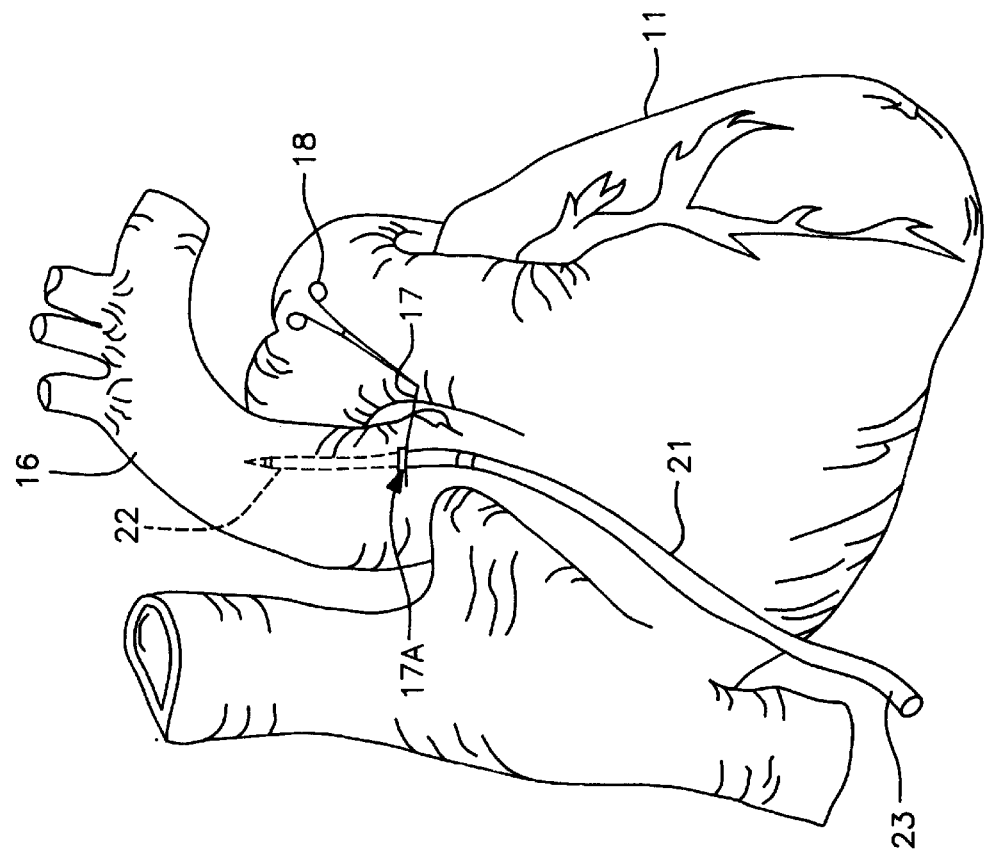
FIGS. 2–3 are schematic views of the patient's heart showing preliminary placement of the cannula apparatus of the present invention.
Figure 3:
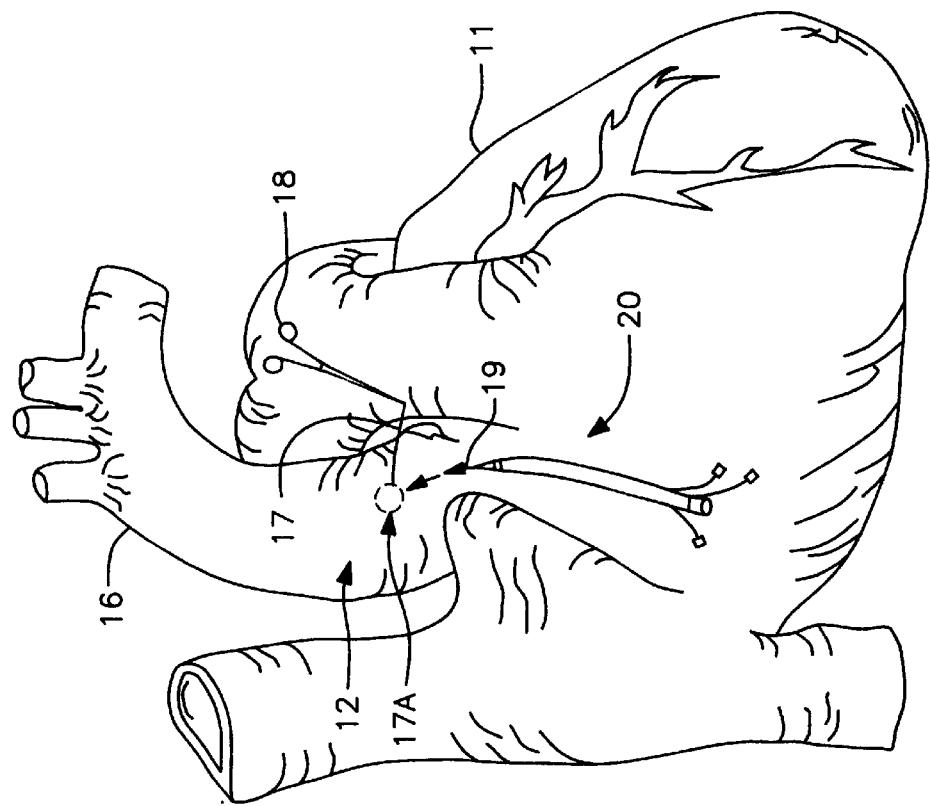

In FIGS. 2–3, the patient's heart 11 is shown with the ascending aorta indicated as 16. Pursestring suture 17 has been shown in FIG. 2, being placed before a surgical incision 17A has been formed in the heart 11 at cannulation site 12. The pursestring suture 17 can be secured using a surgical hemostat 18 or like instrument.

In FIG. 3, the distal end portion 22 of cannula 20 tubular body 21 has been inserted through the incision 17A into the lumen of the patient's ascending aorta 16. The pursestring 17 is tightened using hemostat 18. In FIG. 2, arrow 19 illustrates the insertion distal end portion of body 21 of cannula apparatus 20 through incision 17A into the lumen of aorta 16. Proximal end portion 23 of cannula body 21 is positioned externally of aorta 16 as shown in FIG. 3.

Figure 4:
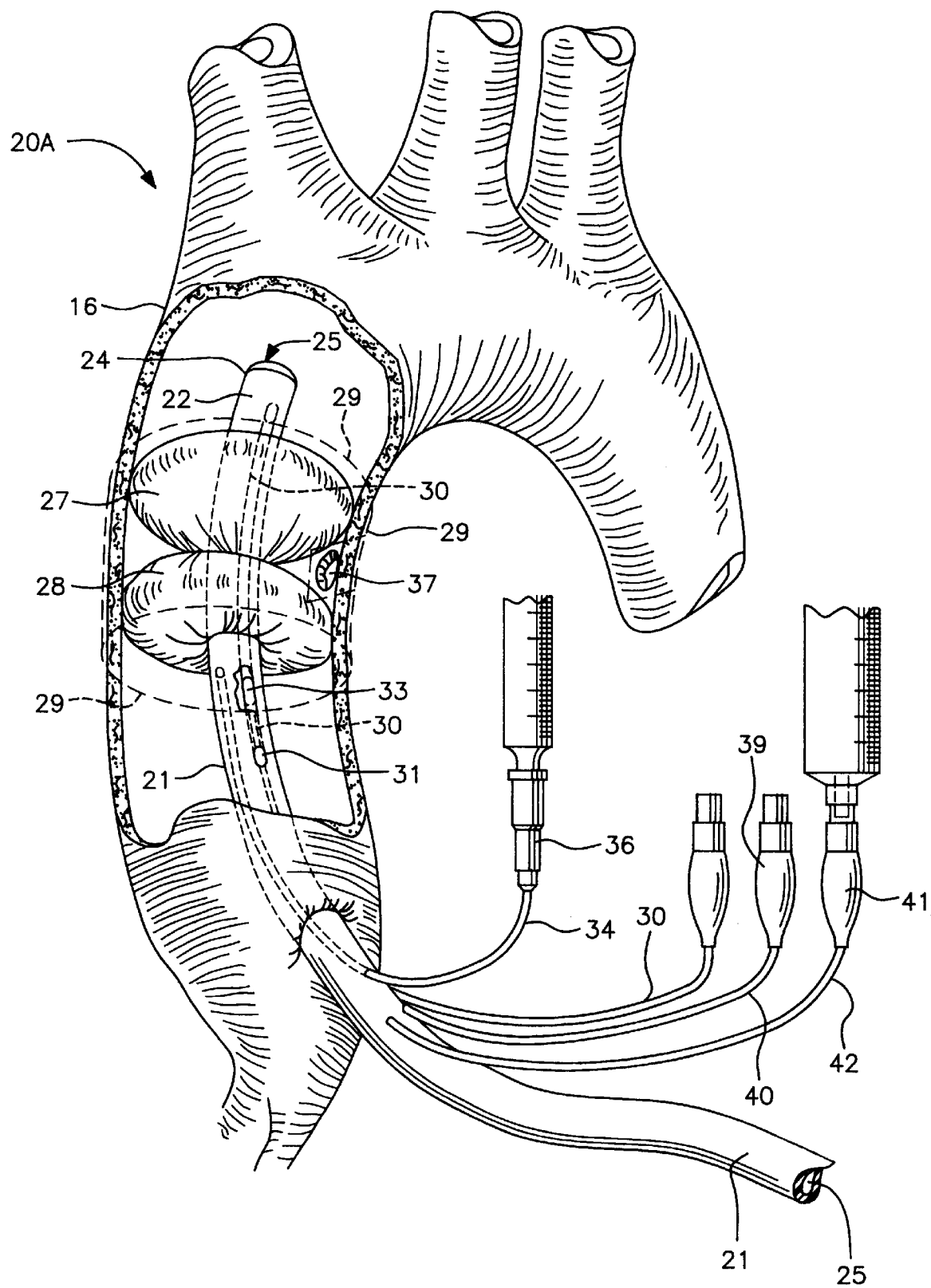
FIG. 4 is a fragmentary perspective view of a first and the preferred embodiment of the apparatus of the present invention after placement in a patient's ascending aorta.
Figure 8:
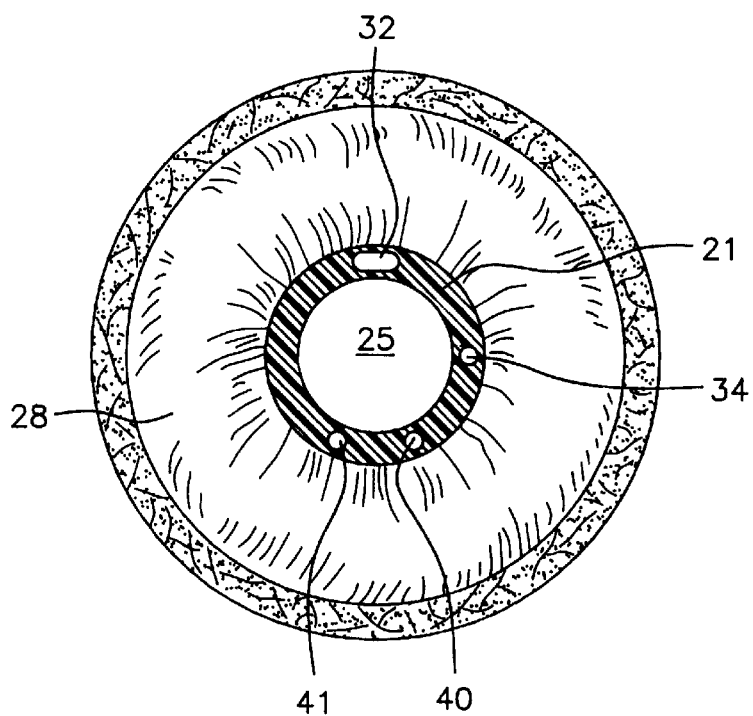
FIG. 8 is a transverse sectional view taken along lines 8—8 of FIG. 7.

In FIG. 4, the distal end portion 22 of cannula tubular body 21 is shown more particularly after placement within the patient's aorta. In FIG. 4, the first and preferred embodiment of the cannula apparatus of the present invention is designated by the numeral 20A. However, it should be understood that the first embodiment of cannula 20 would similarly be placed within the patient's ascending aorta 16 as shown in FIG. 4. Cannulae 20, 20A each provide a distal cannula tip 24 or 24A, a central lumen 25, and a cannula wall 26. Cannula 20 differs in that it provides a pointed tip 24A.

In FIGS. 4, 7A–7B and 8, a pair of balloons 27, 28 are mounted on distal end portion 22 of cannula body 21. The balloon 27 is a total occlusion balloon. The balloon 28 is a partial occlusion balloon. An aortic retaining sleeve 29 is positioned about ascending aorta 16 at a position next to the balloons 27, 28 as shown in FIG. 4. The length of each of the intra aortic occlusive balloons 27, 28 when fully engaged should allow for a contact surface length of 15–30 mm in length. This "footprint" will continue circumferentially along the inner wall of the ascending aorta 16. Thus, the sleeve 29 is of a length L that extends sufficiently to cover both balloons 27 and 28 as shown in FIG. 4. Further, the sleeve 29 has an internal diameter that is sized and shaped to conform to the outside surface of the ascending aorta 16.

During insertion, a partial flow bypass lumen 30 is carefully and completely de-aired upon insertion. The selected cannula 20 or 20A is then positioned within the lumen of the ascending aorta distal to the coronary ostia, and well proximal to the arch vessels at a site that the surgeon decides where the proximal anastamosis will be approximated. The pursestring suture is secured to the cannula body 21 holding it secured in place.

Figure 9A:
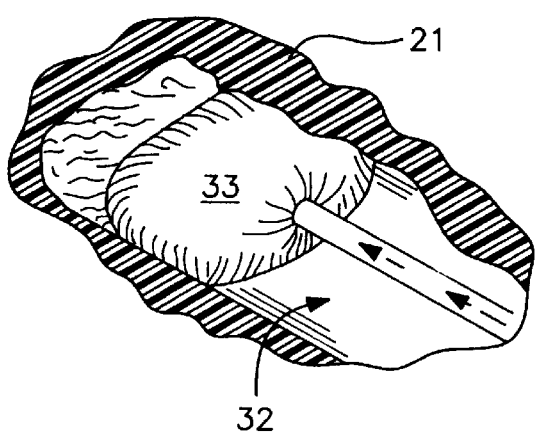
FIGS. 9A–9B are partial fragmentary views of the embodiment of the apparatus of the present invention showing the bypass flow balloon portion thereof.

The partial occlusion balloon 28 is partially inflated and palpated by the surgeon for positive placement. The protective aortic retaining sleeve 29 is then positioned around the aorta 16 as shown in FIG. 4. Placement is verified once more by palpating the partially inflated partial occlusion balloon 28. The partial occlusion balloon 28 is then fully inflated along with the total occlusion balloon 27 while the internal balloon pressures are monitored. At this point, bypass flow port balloon 33 is fully inflated (see FIG. 9A) thereby completely occluding the bypass port 31 and channel 32. This fully isolates the heart 11 from the systemic circulation. The diameter of the partial flow bypass lumen 30 should be of sufficient diameter to accept adequate flows of 1 to 1.5 liters per minute without excessive pressure drop. Occlusive aortic balloons 37, 28 must be filled using only sterile saline solution completely free of any air. The predesignated safe parameters for effective balloon inflation pressures are between about 250 to 400 torr (mm Hg). The aortic occlusion balloon maximum function diameter should be between about 25–50 mm.

Myocardial protecting solution mixture is then delivered to the section of the aorta 16 which is proximal to the occlusive balloons 27, 28. This protective solution mixture is delivered through the cardioplegia delivery channel 34 and the delivery port 35 (see FIGS. 4–5 and 7). The diameter of the cardioplegia delivery channel 34 and cardioplegia delivery port 35 should be of a sufficient diameter to accept without excessive pressure drop a flow of 300–400 ml per minute. Once a full arrest is attained and the antegrade cardioplegia dose has been administered, a controlling stopcock valve 36 is turned so as to allow the aortic root and heart to be vented through the same port and channel 34, 35 that are used to administer myocardial protecting solution.

Figure 9B:
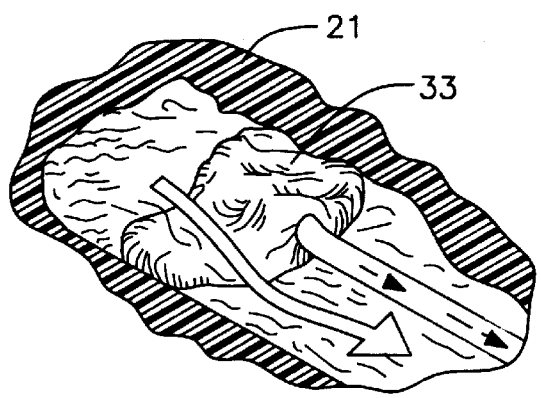
Figure 10A:
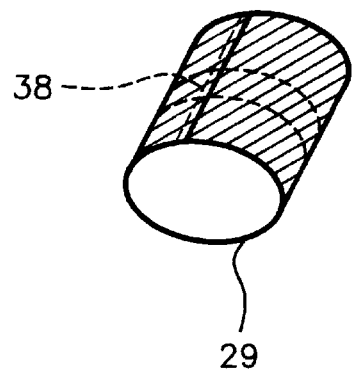
FIGS. 10A–10B are partial perspective view of the preferred embodiment of the apparatus of the present invention illustrating the aortic retaining sleeve portion thereof.
Figure 10B:
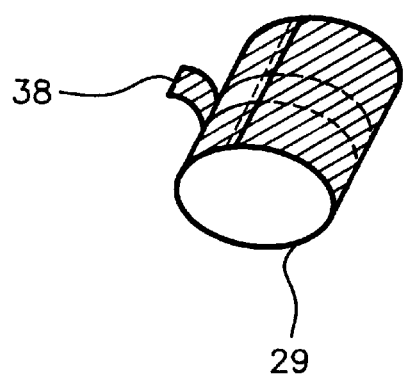

When the surgeon completes the necessary distal anastamosis, the heart and aortic root are filled with blood and completely de-aired. The partial flow bypass balloon 33 is then deflated (see FIG. 9B) and partial bypass is commenced. The surgeon then will complete the proximal anastamosis on the aorta within the region between the partial and total occlusion balloons 27, 28 as shown in FIG. 4 by the numeral 37. The protective aortic sleeve 29 has a removable section 38 (see FIGS. 10A and 10B) that can be peeled away to expose that portion of the aorta that will be the proximal anastamosis site 37 (see FIG. 4). The protective aortic sleeve 29 can be constructed of a flexible synthetic material (i.e., surgical quality polyester) with fine velcro fasteners incorporated along alternating sides of the opposite ends of the sleeve when fully opened. As the last proximal anastamosis is near completion, the partial occlusion balloon 28 is slightly deflated in order to displace any air still proximal to the total occlusion balloon 27.

When all the air has been purged, the partial occlusion balloon 28 is fully deflated to be followed by the deflation of the total occlusion balloon 27.

Figure 11:
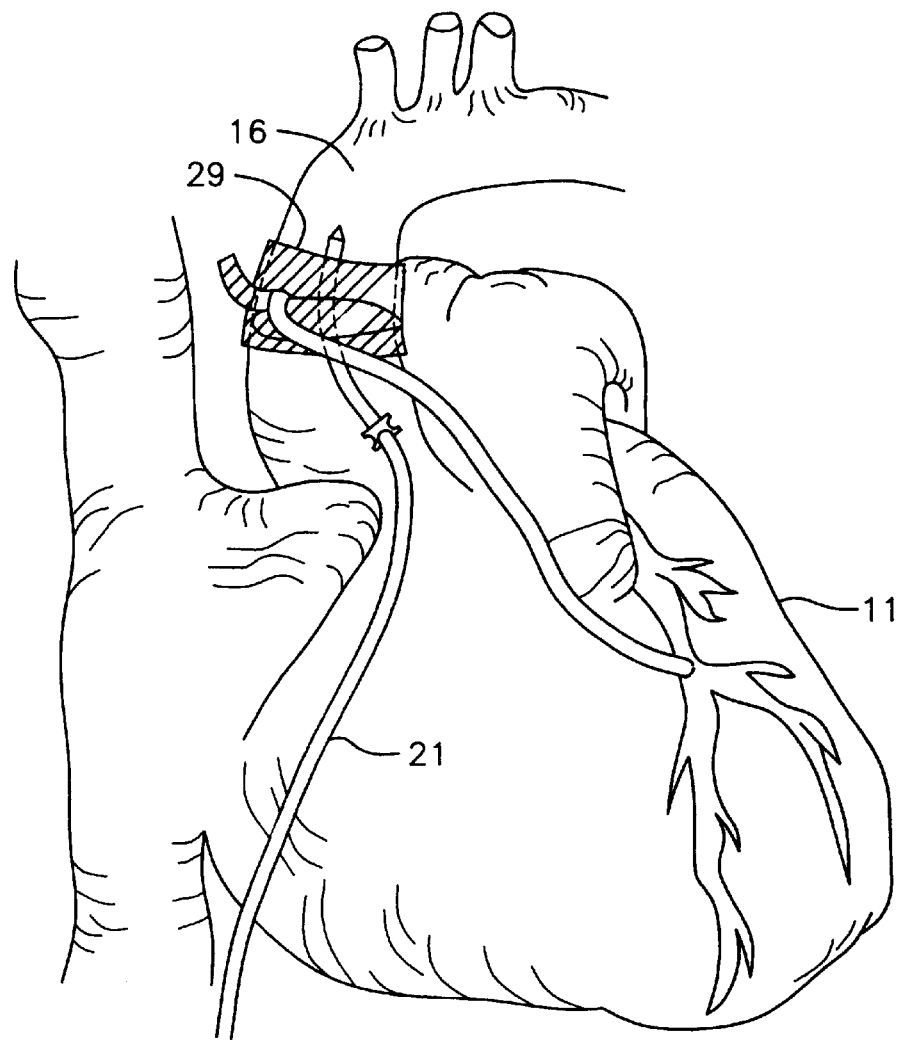
FIG. 11 is a schematic illustration of the patient's heart showing placement of a bypass using the method and apparatus of the present invention.
Figure 13:
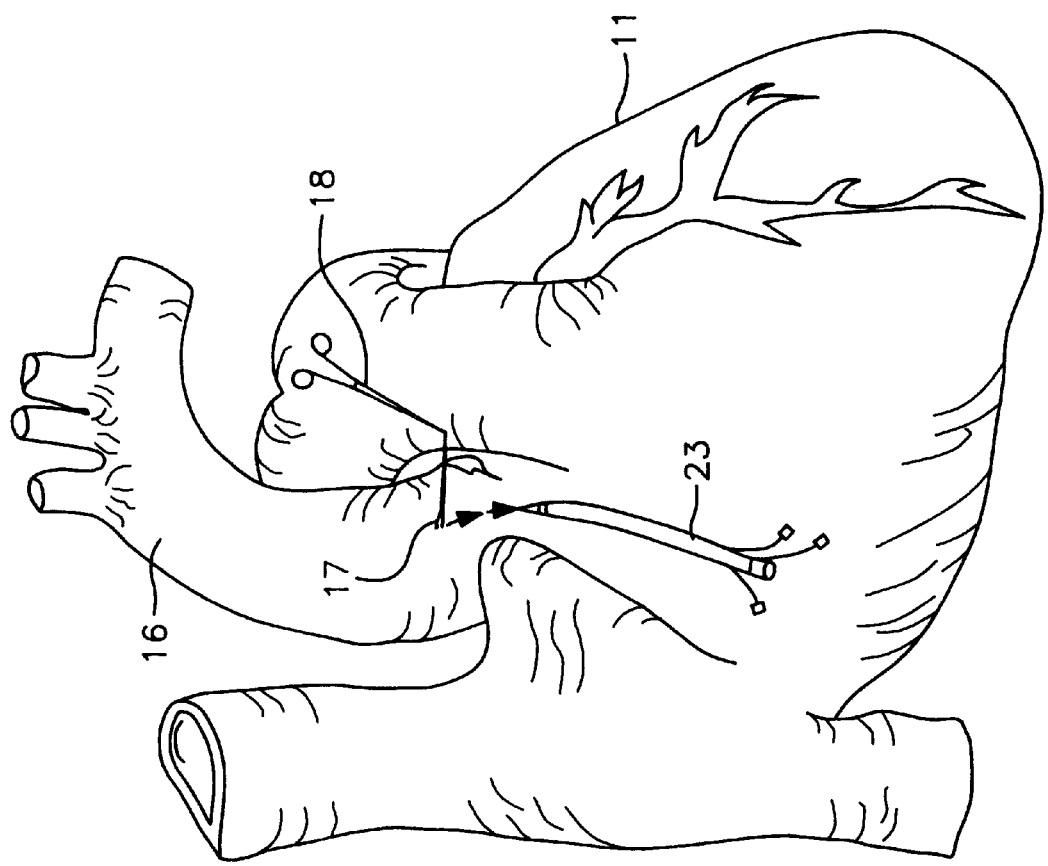
FIG. 13 is a perspective view of the patient's heart illustrating removal of the cannula after heart surgery is complete.
Figure 12:
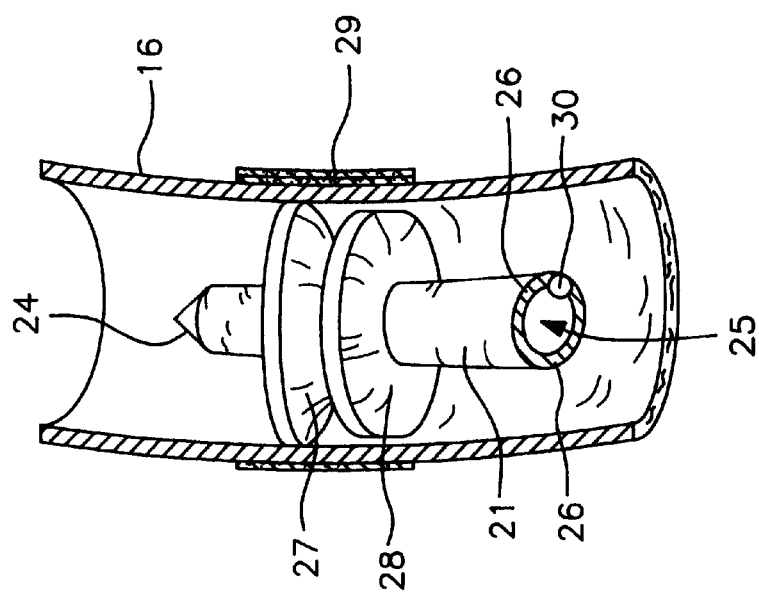
FIG. 12 is a fragmentary sectional view of the preferred embodiment of the apparatus of the present invention illustrating the distal end and double balloon portions thereof.

The cardiac output and graft condition may be evaluated at this time after which the cardiopulmonary bypass is terminated and the fully deflated cannula 20 or 20A is then removed and the pursestring 17 tied off (see FIGS. 11–13). Aortic occlusive balloons 27, 28 are deflated and the partial bypass balloon is secured in the inflated state. The multi-function arterial catheter 10 is then withdrawn slowly and the pursestring suture 17 is closed and secured shut.

Each of the balloons 27, 28 is provided with a fluid delivery tube and an inflation/deflation valve. In FIG. 4, the balloon 27 is provided with inflation/deflation valve 39 and fluid delivery tube 40. The partial occlusion balloon 28 is provided with a fluid delivery tube 42 and an inflation/deflation valve 41.

The following table lists the parts numbers and parts descriptions as used herein and in the drawings attached hereto.

PARTS LIST

| Part Number | Description |
| --- | --- |
| 10 | patient |
| 11 | heart |
| 12 | cannulation site |
| 13 | cardio pulmonary bypass machine |
| 14 | arterial delivery line |
| 15 | venous return line |
| 16 | ascending aorta |
| 17 | pursestring suture |
| 17A | incision |
| 18 | surgical hemostat |
| 19 | arrow |
| 20 | cannula |
| 20A | cannula |
| 21 | tubular body |
| 22 | distal end portion |
| 23 | proximal end portion |
| 24 | distal cannula tip |
| 24A | distal cannula tip |
| 25 | central lumen |
| 26 | cannula wall |
| 27 | total occlusion balloon |
| 28 | partial occlusion balloon |
| 29 | aortic retaining sleeve |
| 30 | partial flow bypass lumen |
| 31 | port |
| 32 | channel |
| 33 | bypass flow balloon |
| 34 | cardioplegia delivery channel |
| 35 | cardioplegia delivery port |
| 36 | flow control stopcock |
| 37 | proximal anastamosis |
| 38 | removable section |
| 39 | inflation/deflation valve |
| 40 | fluid delivery tube |
| 41 | inflation/deflation valve |
| 42 | fluid delivery tube |

The foregoing embodiments are presented by way of example only; the scope of the present invention is to be limited only by the following claims.

What is claimed is:

1. A protective aortic occlusion cannula apparatus for occluding a patient's aorta during open heart surgery, comprising:

a) a cannula body having a wall surrounding a lumen, proximal and distal end portions, the proximal end portion being sized and shaped for surgical placement into a patient's aorta;

b) two separate and equal sized balloons, the balloons being independently inflatable and deflatable, said balloons being positioned on the distal end portion of the catheter body about the wall;

c) the cannula body having channels for carrying fluid to and from the balloons during selected inflation or deflation;

d) wherein each balloon can be partially or fully inflated independently of the other for expanding the balloon to engage the patient's aorta; and e) valves for controlling fluid flow in the channels.

2. The protective aortic occlusion cannula apparatus of claim 1 further comprising a sleeve that fits over the exterior of the patient's aorta at a position next to the balloons for preventing enlargement of the aorta by inflation of the balloons.

3. The protective aortic occlusion cannula apparatus of claim 1 wherein the sleeve is generally cylindrically shaped.

4. The protective aortic occlusion cannula apparatus of claim 1 wherein the sleeve has a removable portion that enables a surgeon to access the aorta at the sleeve and in between the balloons.

5. The protective aortic occlusion cannula apparatus of claim 1 wherein the two balloons are spaced longitudinally along the cannula body.

6. The protective aortic occlusion cannula apparatus of claim 1 wherein the two balloons are spaced longitudinally, providing a recess therebetween.

7. The protective aortic occlusion cannula apparatus of claim 1 wherein the balloons each have a periphery, the respective balloon peripheries being spaced longitudinally, providing a recess therebetween.

8. The protective aortic occlusion cannula apparatus of claim 1 wherein each of the balloons has a periphery that engages the aorta forming a seal therewith when the balloons are inflated.

* * * * *